US00PP24548P2

(12) United States Plant Patent
Kordes

(10) Patent No.: US PP24,548 P2
(45) Date of Patent: Jun. 17, 2014

(54) CLIMBING ROSE PLANT NAMED 'KORTEHABA'

(50) Latin Name: *Rosa hybrida*
Varietal Denomination: KORtehaba

(75) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/507,404

(22) Filed: Jun. 26, 2012

(51) Int. Cl.
*A01H 5/00* (2006.01)

(52) U.S. Cl.
USPC ..... Plt./109

(58) Field of Classification Search
USPC ..... Plt./114, 109
See application file for complete search history.

*Primary Examiner* — Kent L Bell

(57) ABSTRACT

A new and distinct variety of rose with long lasting, novel pink flowers with yellow centers, and attractive foliage with excellent disease resistance. It exhibits upright, arching, moderately vigorous growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORtehaba'. The new variety of rose plant of the present invention originated from a controlled crossing in a breeding program of two distinct parents during the summer of 2001. The crossing was between an "un-named seedling", the seed parent, and another "un-named seedling", the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtehaba'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an "un-named seedling", by the following combination of characteristics:

1. 'KORtehaba' has pink flowers with yellow centers and a climbing growth habit, whereas the "un-named seedling" has dark red flowers and a bushy, arching growth habit.
2. 'KORtehaba' has better disease resistance than the "un-named seedling".

The new rose plant may be distinguished from its pollen parent, an "un-named seedling", by the following combination of characteristics:

1. 'KORtehaba' has semi-double pink flowers with yellow centers, whereas the "un-named seedling" has single yellow flowers.

2. 'KORtehaba' has a climbing growth habit, whereas the "un-named seedling" has a compact growth habit.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORtehaba' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtehaba' was selected in May, 2002 from the seedling beds to be asexually propagated for further evaluation. The first asexual propagation of 'KORtehaba' was done by budding to seedling understocks in July, 2002 at the inventor's nursery in Offenseth-Sparrieshoop, Germany.

This initial and other subsequent propagations conducted in controlled environments demonstrate that 'KORtehaba' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, fruit, leaves, prickles, and stems of 'KORtehaba'.

DETAILED BOTANICAL DESCRIPTION

The following is a description of 'KORtehaba', as observed growing in October, 2011 in a nursery in Jackson County, Oreg. on plants 3 years of age. Color references are made using The Royal Horticultural Society (London, England) Colour Chart, 2001 except where common terms of color are used.

For a comparison, several physical characteristics of the rose variety 'KORgolgat', a rose variety from the same inventor described and illustrated in U.S. Plant Pat. No. 17,376 and issued on Jan. 23, 2007 are compared to 'KORtehaba' in Chart 1.

CHART 1

| Characteristic | 'KORtehaba' | 'KORgolgat' |
|---|---|---|
| Petal count | 8-10 | 55-60 |
| Pistil count | 25 | 45-55 |
| Outermost petal color after opening, inner side | Red Group 50A | Yellow Group 12A |

Parents:

*Seed parent*.—An "un-named seedling".

*Pollen parent*.—An "un-named seedling".

Classification:

*Botanical classification*.—*Rosa hybrida* 'KORtehaba'.

*Commercial classification*.—Climbing rose.

FLOWER AND FLOWER BUD

Blooming habit: Recurrent.

Flower bud:

*Size*.—Upon opening, 18 mm in length from base of receptacle to distal end of bud and 10 mm diameter at its widest point.

*Bud form*.—Short. Pointed ovoid.

*Bud color*.—As sepals first unfold, bud color is Red Group 46B. When ¼ open, the upper surface of petals is Red Group 46C and Red Group 38B with Yellow Group 11B in the basal zone, and the lower surface is Red Group 46B.

*Sepals*.—Color: Upper surface Yellow-Green Group 144C. Lower surface Yellow-Green Group 146D. Intonations of Greyed-Purple Group 185B. Size: Average 20 mm (l)×8 mm (w). Shape: Very weak foliaceous appendages on 3 of the five sepals. Apex: Apiculate. Base: Flat at union with receptacle. Quantity: Five. Surface texture: Upper side: Pubescent with stipitate glands. Lower surface: Lightly pubescent with stipitate glands. Margins: Pubescent with stipitate glands.

Receptacle:

*Surface*.—Smooth with a few stipitate glands at the base.

*Color*.—Yellow-Green Group 144D.

*Shape*.—Urn-shaped.

*Size*.—8 mm (h)×8 mm (w).

Peduncle:

*Surface*.—Smooth with stipitate glands.

*Length*.—20 to 25 mm average length.

*Diameter*.—1.0 to 1.5 mm average diameter.

*Color*.—Yellow-Green Group 144B.

*Strength*.—Strong.

*Borne*.—Multiple flower buds per stem, generally 3 to 6.

Flower bloom:

*Fragrance*.—None.

*Duration*.—On the plant 5 to 8 days. As a cut flower, 3 to 5 days. Senesced petals drop away cleanly.

*Size*.—Medium for a climbing rose. When open, the average flower diameter is 70 mm and the average flower height is 10 mm.

*Form*.—Shape of flower when viewed from the side: Upon opening, upper part: Flat. Upon opening, lower part: Flattened convex. Open flower, upper part: Flattened convex. Open flower, lower part: Concave.

Color:

*Upon opening, petals*.—Outermost petals: Outer Side: Red Group 46B and Red Group 46C in marginal and middle zones, Yellow 13C in basal zone. Inner Side: Red Group 46D. Innermost petals: Outer Side: Greyed-Orange Group 170D. Inner Side: Red Group 45B.

*Upon opening. basal petal spots*.—Basal petal spot, outermost petals: Outer Side: Yellow Group 9B. Inner Side: Yellow Group 7B. Basal petal spot, innermost petals: Outer Side: Yellow Group 6B. Inner Side: Green-Yellow Group 1B.

*After opening, petals*.—Outermost petals: Outer Side: Orange Group 27B with intonations of Yellow-Orange Group 20B in middle zone and Red Group 39B in marginal zone. Inner Side: Red Group 50A. Innermost petals: Outer Side: Orange Group 27B with intonations of Yellow-Orange Group 20B in middle zone and Red Group 39B in marginal zone. Inner Side: Red Group 50A.

*After opening, basal petal spots*.—Basal petal spot, outermost petals: Outer Side: Yellow Group 9B. Inner Side: Yellow Group 2A. Basal petal spot, innermost petals: Outer Side: Yellow Group 9C. Inner Side Yellow Group 2A.

General tonality: On open flower Red Group 50A. No change in the general tonality at the end of the third day. Afterwards, general tonality is Red Group 51 A.

Petals:

*Petal count*.—Semi-double.

*Average range*.—Approximately 8 to 10 petals under normal conditions.

*Petal reflex*.—Petals reflex slightly.

*Petal edge*.—Ruffled.

*Petal shape*.—Obtuse. Apex shape is obtuse. Shape of base is obtuse.

*Petal size*.—30-40 mm (l) 25-30 mm (w).

*Thickness*.—Thin.

*Petal arrangement*.—Not formal.

Petaloids:

*Petaloid count*.—Average of 0 to 3 per flower.

*Petaloid size*.—Petaloids are 15-25 mm (l) and 5-20 mm (w).

*Petaloid color*.—Color of inner side is Red Group 53B. Color of outer side is Orange Group 27A.

*Petaloid texture*.—Average.

*Margins*.—Entire, with some highly irregular.

*Petaloid shape*.—Obovate. Apex: Obtuse. Base: Attenuate.

Reproductive organs:

*Pistils*.—Abundant. Approximately 25 present. Stigmas: Location: Slightly inferior in position to anthers. Color: Green-Yellow Group 160C. Styles: Length: About 4 mm long. Color: Green-Yellow Group 160C.

*Stamens*.—Approximately 60 on average and regularly arranged. Anthers: Size: Average 1 mm long. Pollen: Generally present. Color: Yellow-Orange Group 22A. Filaments: Color: Yellow Group 12A. Length: 5-10 mm.

THE PLANT

Growth: Moderate.

Plant habit: Upright, arching habit. When grown as a budded field plant on *Rosa multiflora* understock, the average plant height is 250 cm and the average plant width is 125 cm.

Stems:

*Stem color*.—Young wood: Yellow-Green Group 146B. Older wood: Yellow-Green Group 146D.

*Stem surface*.—Young wood: Smooth. Older wood: Smooth.

Prickles: Present.

*Incidence*.—Average of 8 per each 10 cm of stem.

*Size*.—Average length: 5 mm.

*Color*.—Immature prickles: Greyed-Purple Group 185A. Mature prickles: Greyed-Orange Group 134C. Senescing to Greyed-White Group 156D.

*Shape*.—Concave.

Leaves and leaflets: Normally 7 leaflets on normal leaves in middle of the stem.

*Venation pattern*.—Pyramidal net pattern.

*Leaf size*.—110 mm (l)×75 mm (w).

*Abundance*.—Average.

*Texture*.—Smooth. Upper side of leaflet: Semi-glossy. Under side of leaflet: Matte. Stipitate glands present on lower bottom of leaflet.

*Color, mature foliage*.—Upper Leaf Surface: Green Group 137B. Lower Leaf Surface: Yellow-Green Group 146D.

*Color, juvenile foliage*.—Upper Leaf Surface: Green Group 137A. Lower Leaf Surface: Green Group 137C.

*Anthocyanin intonation*.—Present. Intonations present on leaflet margins and leaf attachments: Greyed-Purple Group 183B.

Stipules:

*Size*.—10 mm long, 5 mm from distal tip to distal tip.

*Stipule color*.—Yellow-Green Group 146D.

*Anthocyanin*.—Greyed-Purple Group 184D on upper center.

*Margins*.—With stipitate glands.

*Shape*.—Apex: Apiculate. Base: Flat.

Petiole:

*Length*.—Average 10 mm.

*Diameter*.—Average 1.5-2.0 mm.

*Petiole color*.—Yellow-Green Group 146C.

*Underneath*.—With stipitate glands.

*Margins*.—With stipitate glands and fine hairs.

*Anthocyanin*.—Greyed-Purple Group 183B on immature foliage.

*Stipitate glands*.—In center of upper side.

Petiole rachis:

*Length*.—Average 15 mm.

*Diameter*.—Average 1.5 mm.

*Color*.—Yellow-Green Group 146C. Anthocyanin present on juvenile tissue: Greyed-Purple Group 183B.

*Margins*.—With stipitate glands.

*Prickles*.—Small, fine prickles underneath of Greyed-Purple Group 183B.

*Stipitate glands*.—Abundant stipitate glands on upper and lower surfaces.

Leaflets:

*Size*.—Average size of the terminal leaflet is 40-50 mm (l)×20-25 mm (w).

*Shape*.—Ovate. Base: Obtuse. Apex: Acute.

*Margins*.—Serrated.

*Surface*.—Upper: Semi-glossy. Lower: Matte.

*Texture*.—Smooth.

*Arrangement*.—Odd pinnate.

Hips/seed formation: Color of mature hips: Greyed-Orange Group 171B. Size: 25 mm (l)×25 mm (w).

Winter hardiness: To date, the variety has been grown successfully in USDA zones 6-9.

Disease resistance: Excellent resistance to Powdery mildew (*Sphaerotheca pannosa*) and blackspot (*Diplocarpon rosae* diseases under normal growing conditions.

I claim:

1. A new and distinct variety of rose plant, as described and illustrated herein.

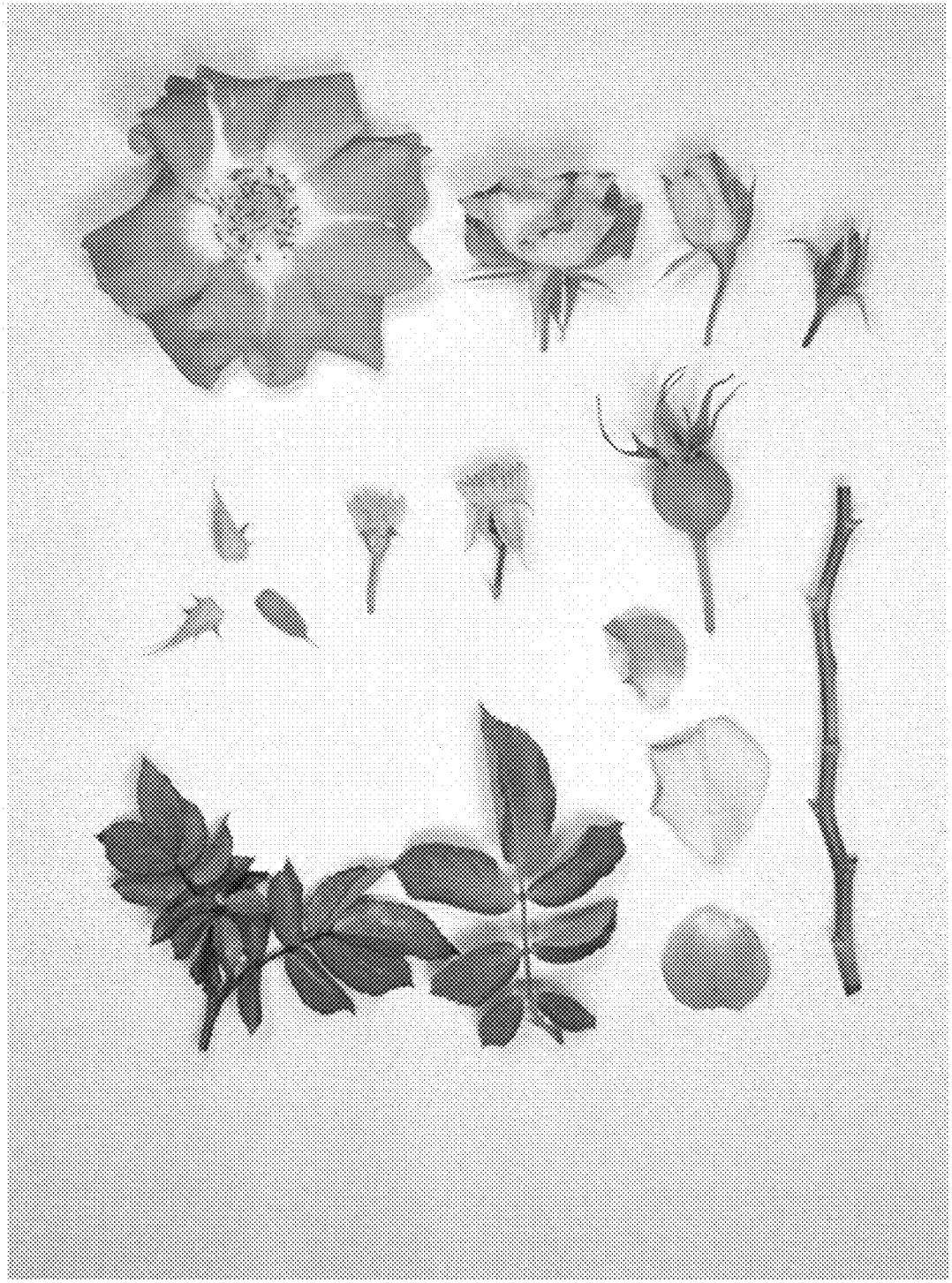

* * * * *